(12) United States Patent
Yan et al.

(10) Patent No.: US 9,993,304 B2
(45) Date of Patent: Jun. 12, 2018

(54) VISUALIZATION OF CATHETER OF THREE-DIMENSIONAL ULTRASOUND

(75) Inventors: Pingkun Yan, Bethesda, MD (US);
Vijay Parthasarathy, Tarrytown, NY (US); Robert Manzke, Bonebuttel (DE); Ameet Kumar Jain, New York, NY (US)

(73) Assignee: Koninklijke Philips N.V., Eindhoven (NL)

( * ) Notice: Subject to any disclaimer, the term of this patent is extended or adjusted under 35 U.S.C. 154(b) by 681 days.

(21) Appl. No.: 13/997,800

(22) PCT Filed: Jan. 10, 2012

(86) PCT No.: PCT/IB2012/050109
§ 371 (c)(1),
(2), (4) Date: Jun. 25, 2013

(87) PCT Pub. No.: WO2012/095784
PCT Pub. Date: Jul. 19, 2012

(65) Prior Publication Data
US 2013/0281839 A1 Oct. 24, 2013

Related U.S. Application Data

(60) Provisional application No. 61/432,327, filed on Jan. 13, 2011.

(51) Int. Cl.
*A61B 34/20* (2016.01)
*A61B 6/12* (2006.01)
(Continued)

(52) U.S. Cl.
CPC .............. *A61B 34/20* (2016.02); *A61B 6/12* (2013.01); *A61B 8/0883* (2013.01); *A61B 8/466* (2013.01); *A61B 8/483* (2013.01)

(58) Field of Classification Search
None
See application file for complete search history.

(56) References Cited

U.S. PATENT DOCUMENTS

| 4,930,519 A | 6/1990 | Anderson et al. |
| 6,389,104 B1 | 5/2002 | Bani-Hashemi et al. |
(Continued)

FOREIGN PATENT DOCUMENTS

| DE | 10210648 | 10/2003 |
| DE | 102007021061 A1 | 11/2008 |
| WO | WO2005092198 | 10/2005 |

OTHER PUBLICATIONS

Uherčík, Marián, et al. "Model fitting using ransac for surgical tool localization in 3-d ultrasound images." IEEE Transactions on Biomedical Engineering 57.8 (2010): 1907-1916.*

*Primary Examiner* — Amelie R Gillman
*Assistant Examiner* — Carolyn Pehlke

(57) ABSTRACT

An image-guided system includes an X-ray imaging device for generating one or more X-ray images illustrating a tool within an anatomical region, and an ultrasound imaging device for generating an ultrasound image illustrating the tool within the anatomical region. The image-guided system further includes a tool tracking device for visually tracking the tool within the anatomical region. In operation, the tool tracking device localizes a portion of the tool as located within the ultrasound image responsive to an identification of the portion of the tool as located within the X-ray image(s), and executes an image segmentation of an entirety of the tool as located within the ultrasound image relative to a localization of the portion of the tool as located within the ultrasound image.

15 Claims, 11 Drawing Sheets

(51) Int. Cl.
*A61B 8/08* (2006.01)
*A61B 8/00* (2006.01)

(56) References Cited

U.S. PATENT DOCUMENTS

| | | |
|---|---|---|
| 2001/0029334 A1 | 10/2001 | Graumann et al. |
| 2003/0199748 A1 | 10/2003 | Camus et al. |
| 2003/0220561 A1 | 11/2003 | Camus et al. |
| 2005/0134587 A1* | 6/2005 | Geiger et al. ................ 345/423 |
| 2006/0064006 A1 | 3/2006 | Strommer et al. |
| 2007/0014473 A1* | 1/2007 | Slabaugh et al. ............ 382/173 |
| 2007/0015996 A1 | 1/2007 | Camus et al. |
| 2007/0160277 A1* | 7/2007 | Slabaugh et al. ............ 382/128 |
| 2007/0276243 A1 | 11/2007 | Gerard et al. |
| 2008/0199059 A1 | 8/2008 | Eck et al. |
| 2008/0234570 A1 | 9/2008 | Gerard et al. |
| 2009/0136103 A1 | 5/2009 | Sonka et al. |
| 2009/0326373 A1 | 12/2009 | Boese et al. |
| 2010/0063400 A1 | 3/2010 | Hall et al. |

\* cited by examiner

VISUALIZATION OF CATHETER OF THREE-DIMENSIONAL ULTRASOUND

The present invention generally relates to accurate image guidance for an interventional procedure, particularly an interventional cardiac procedure. The present invention specifically relates to visualization of an interventional tool (e.g., a catheter) in an ultrasound image ("3D US").

Knowing a relative position of an interventional tool (e.g., a catheter) with respect to a pre-procedural planning scan (e.g., a magnetic resonance imaging ("MRI") scan or a computed tomography ("CT") scan) is important for accurate guidance in an interventional procedure, particularly an interventional cardiac procedure. Since X-ray fluoroscopic images provide very highly resolved images of the interventional tool during the procedure, image-guided systems known in the art for providing visual aid in guiding the interventional tool have concentrated on tracking a tip of the tool in fluoroscopic images and overlaying in the pre-procedural scan. It is also well known, for visualization of a 3D shape of the interventional tool in real time, to mount a multitude of position sensors and/or shape sensing sensors on the interventional tool in order to track the 3D shape of the interventional tool.

Increasingly, registering an ultrasound image ("2D US") or 3D US with X-ray imaging has augmented X-ray fluoroscopy as an aid for guiding an interventional procedure. The key role of the 2D US or the 3D US is to augment the pre-procedural scan with real time motion information, while the X-ray fluoroscopic image(s) provide high resolution visualization of the interventional tool in real time. Moreover, with the introduction of 3D US in real time, it is becoming possible to visualize the interventional tool more clearly in ultrasound, thereby enabling ultrasound-only guided interventions.

In cardiac interventional procedures, it is important to visualize the tip of a catheter as well as the orientation of the tip of the catheter. The identification of the catheter tip is difficult in 3D US, especially in a cardiac interventional setting. Therefore, methods for identifying the catheter tip in X-ray images and mapping these points into 3D US for extraction and fusing in a pre-procedural scan is beneficial for the interventional procedure.

One form of the present invention is an image-guided system employing an X-ray imaging device (e.g., monoplane or biplane) for generating one or more X-ray images illustrating a tool within an anatomical region (e.g., a catheter within a cardiac region), and an ultrasound imaging device for generating an ultrasound image illustrating the tool within the anatomical region.

The image-guided system further employs a tool tracking device for visually tracking the tool within the anatomical region. In operation, the tool tracking device localizes a portion of the tool (e.g., a tip of the catheter) as located within the ultrasound image responsive to an identification of the portion of the tool as located within the X-ray image(s), and executes an image segmentation (e.g., a graph cut segmentation) of an entirety of the tool as located within the ultrasound image relative to a localization of the portion of the tool as located within the ultrasound image.

A second form of the present invention is an image-guided method for visually tracking a tool within an anatomical region. The method involves a generation of one or more X-ray images illustrating the tool within an anatomical region (e.g., a catheter within a cardiac region), and a generation of an ultrasound image illustrating the tool within the anatomical region.

The method further involves a localization of a portion of the tool (e.g., a tip of the catheter) as located within the ultrasound image responsive to an identification of the portion of the tool as located within the X-ray image(s), and an execution of an image segmentation (e.g., a graph cut segmentation) of an entirety of the tool as located within the ultrasound image relative to a localization of the portion of the tool as located within the ultrasound image.

The foregoing forms and other forms of the present invention as well as various features and advantages of the present invention will become further apparent from the following detailed description of various exemplary embodiments of the present invention read in conjunction with the accompanying drawings. The detailed description and drawings are merely illustrative of the present invention rather than limiting, the scope of the present invention being defined by the appended claims and equivalents thereof.

As previously stated, the present invention provides various methods for visualizing a three-dimensional shape of the interventional tool in real time inside of a three-dimensional pre-procedural planning scan. As will be appreciated by those having ordinary skill in the art from the following descriptions of FIGS. 1-13, these methods are implemented by a tool tracking device of the present invention utilizing X-ray images and ultrasound images. For purposes of facilitating an understanding of the present invention, the tool tracking device will be described herein for tracking a catheter during a cardiac interventional procedure.

Figure 1:
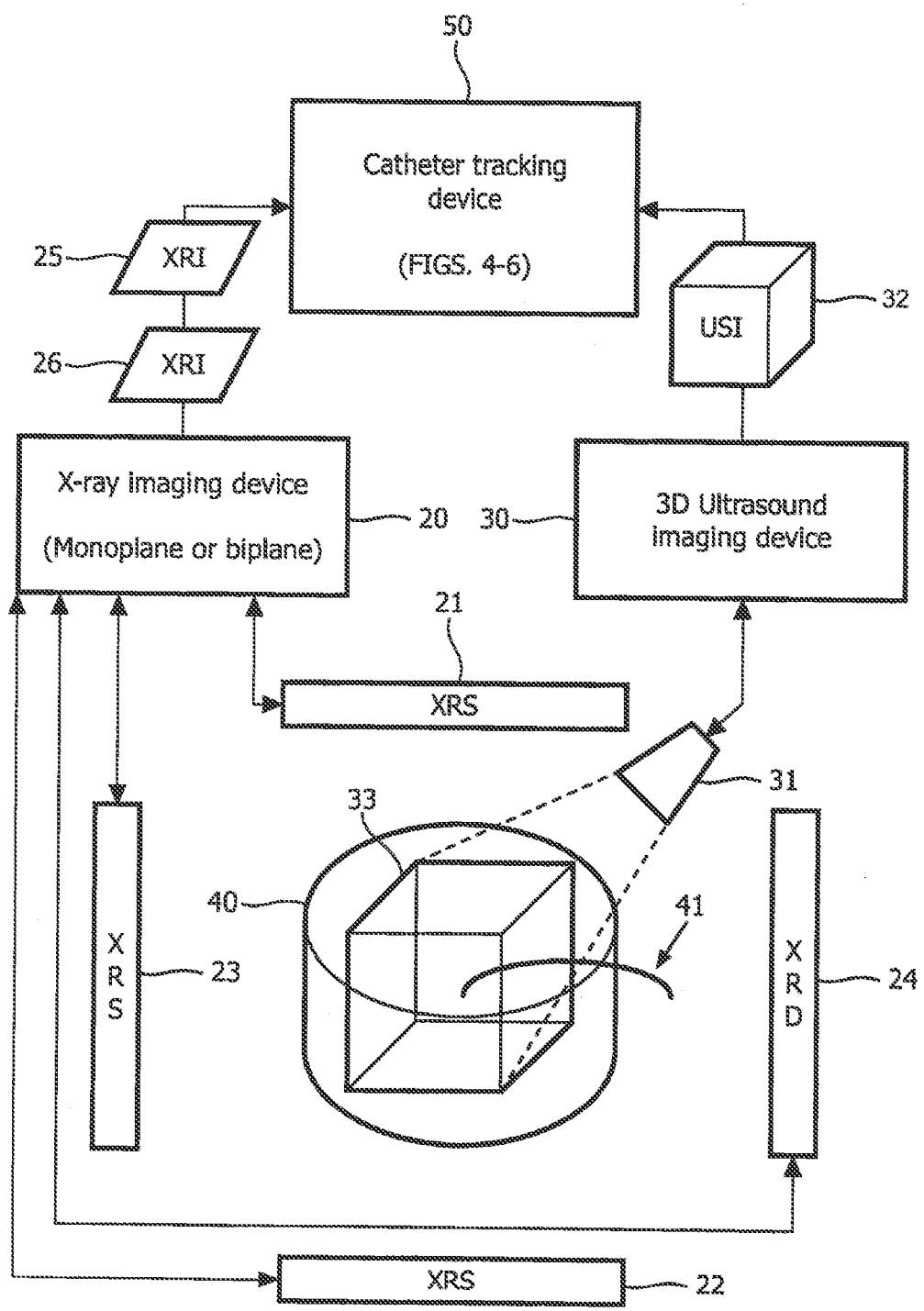
FIG. 1 illustrates an exemplary embodiment of an image-guided system in accordance with present invention.

Specifically, FIG. 1 illustrates an image-guiding system employing an X-ray imaging system, a 3D US imaging system and a tool tracking device in the form of a catheter tracking device 50.

For purposes of the present invention, the X-ray imaging system is broadly defined herein as including an X-ray imaging device 20 for controlling an operation of an X-ray source 21 and an X-ray detector 22 structurally configured for generating a X-ray image ("XRI") 25 of an anatomical region (e.g., a cardiac region) represented by a volume 40 and/or for controlling an operation of an X-ray source 23 and an X-ray detector 24 structurally configured for generating a X-ray image ("XRI") 26 of anatomical region 40. In practice, components 20-22 exclusive of components 23 and 24 represent a monoplane X-ray system of any type, and components 21-24 collectively represent a bi-plane X-ray system of any type. Examples of the X-ray imaging system include, but are not limited to, any type of X-ray system for performing a cardiac interventional procedure. In one embodiment, an X-ray system from the Allure Xper™ series commercially sold by Philips Medical Systems may serve as the X-ray imaging system.

For purposes of the present invention, the 3D US imaging system is broadly defined herein as including 3D US imaging device 30 for controlling an operation of 3D US probe 31 structurally configured for generating an ultrasound image CUSP) 32 of anatomical region 40. Examples of the 3D US imaging system include, but are not limited to, any type of ultrasound imaging system, particularly one utilizing a 3D TEE probe. In one embodiment, the IEEE Intelligent Echo System commercially sold by Philips Medical Systems may serve as 3D US imaging system.

For purposes of the present invention, catheter tracking device 50 is broadly defined herein as any device structurally configured for registering X-ray image(s) 25/26 and ultrasound image 32 for purposes of identifying a tip of a catheter 41 within anatomical region 40, and for visualizing a 3D shape of catheter 41 in real time inside of a 3D pre-procedural planning scan inclusive of anatomical region 40. To this end, catheter tracking device 50 executes an image-guided method represented by a flowchart 60 as shown in FIG. 2.

Figure 2:
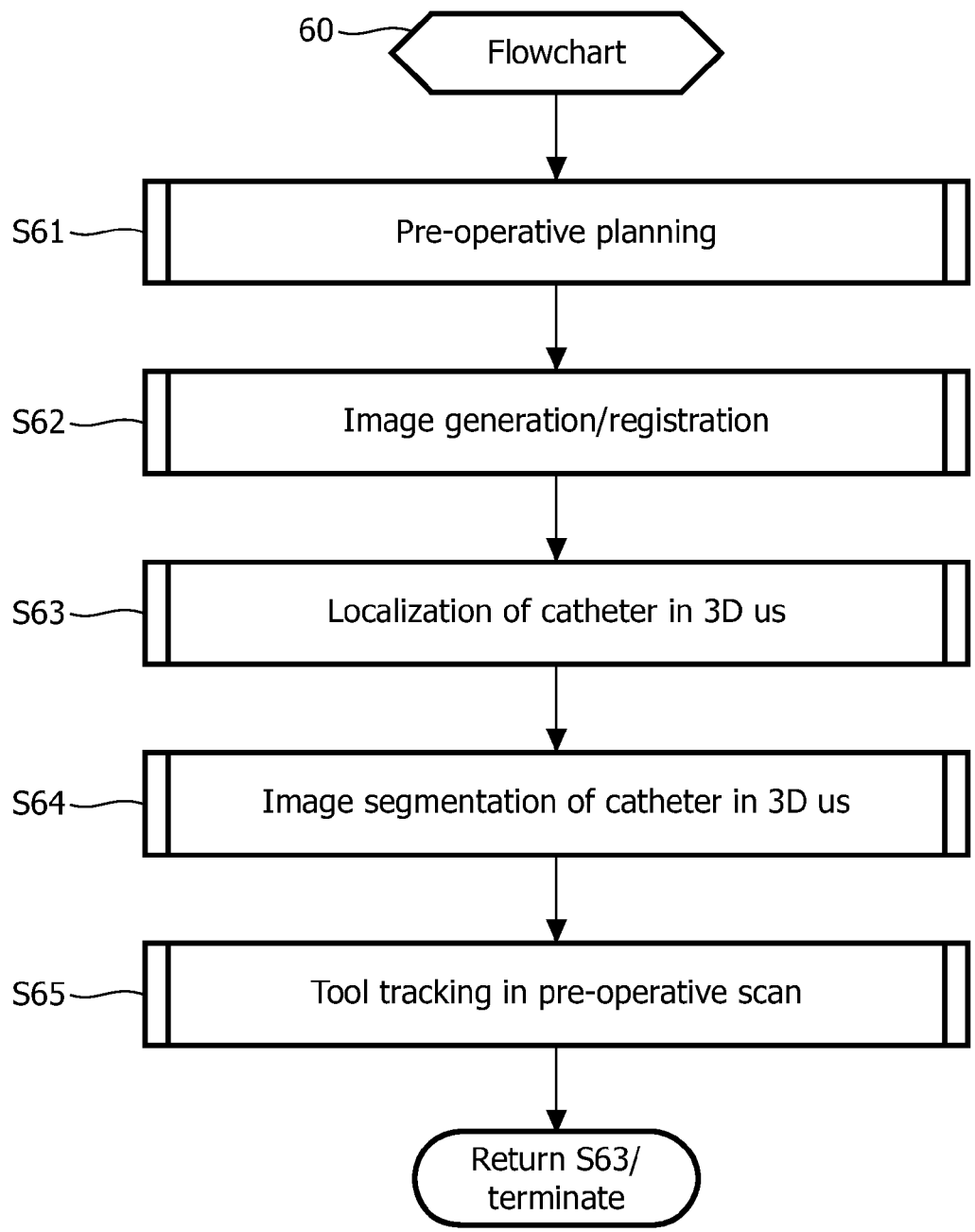
FIG. 2 illustrates a flowchart representative of an image-guided method in accordance with the present invention.
Figure 3:
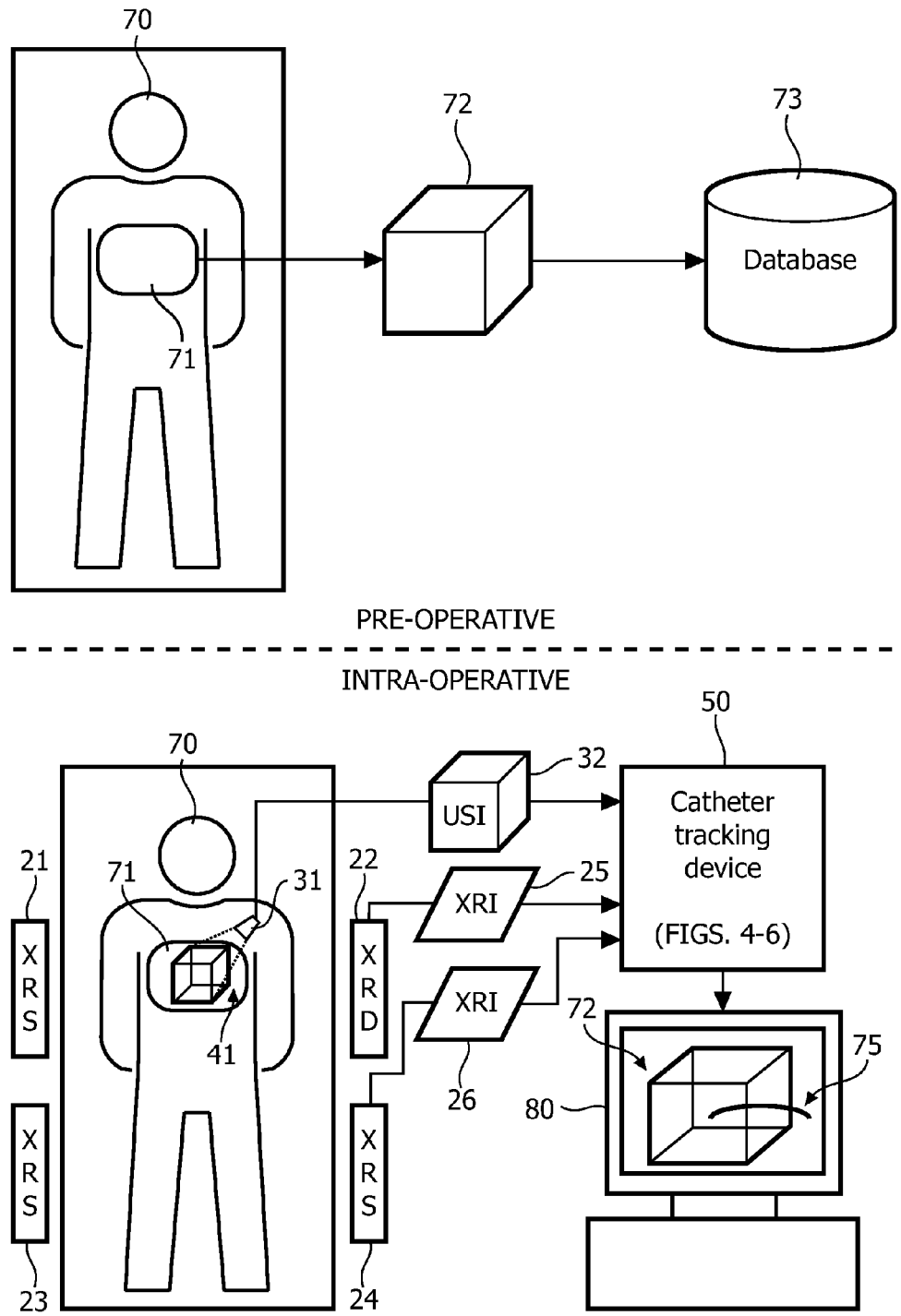
FIG. 3 illustrates an exemplary implementation of the image-guided method of FIG. 2 by the image-guided system of FIG. 1.

Referring to FIG. 2, a stage S61 of flowchart 60 encompasses a pre-operative planning of an interventional procedure involving a 3D scan (e.g., a MRI scan or a CT scan) of an anatomical region of a patient. For example, as shown in FIG. 3, stage S61 may encompass a 3D pre-procedural scan 72 of a cardiac region 71 of a patent 70 and a storage of 3D pre-procedural scan 72 within a database 73.

A stage S62 of flowchart 60 encompasses a registration by catheter tracking device 50 of X-ray image(s) and an ultrasound image of the anatomical region of the patient. For example, as shown in FIG. 3, X-ray image 25 and/or X-ray image 26 of cardiac region 71 as well as ultrasound image 32 of cardiac region 71 are generated by the X-ray imaging system and the 3D US imaging system, respectively, whereby catheter tracking device 50 registers X-ray image 25 and/or X-ray image 26 to ultrasound image 32. In practice, the registration may be involved a conversion of X-ray coordinates into 3D US real-time coordinates using a combination of system calibration and real-time tracking as known in the art. For example, the registration may include manual alignment or an electromagnetic tracking technique.

A stage S63 of flowchart 60 encompasses an identification of a portion of the catheter (e.g., a tip of the catheter) within the ultrasound image. In one embodiment as related to FIG. 3, stage S63 involves an automatic or a manual identification of the tip of catheter 41 within X-ray image 25 and/or X-ray image 26 and a localization of the tip of catheter 41 within ultrasound image 32 derived the X-ray/3D US registration as known in the art.

A stage S64 of flowchart 60 encompasses an image segmentation of catheter 41 within ultrasound image 33 with the catheter tip serving as an initialization point for the image segmentation process.

A stage S65 of flowchart 60 encompasses a tracking of the catheter within a pre-procedural scan of the anatomical region derived from the image segmentation of the 3D shape of the catheter within the ultrasound image. For example, as shown in FIG. 3, stage S65 involves catheter tracking device 50 displaying 3D pre-procedural scan 72 on a display 80 with a tracking overlay 75 of catheter 41 projected within scan 72 as derived from previous image segmentation of the 3D shape of catheter 41 within the ultrasound image 32.

A description of FIGS. 4-13 will now be provided herein to provide a detailed explanation of various embodiments of a catheter tracking device of the present invention including modules structurally configured with hardware, software and/or firmware for implementing stages S63 and S64 of flowchart 60 (FIG. 2).

Figure 4:
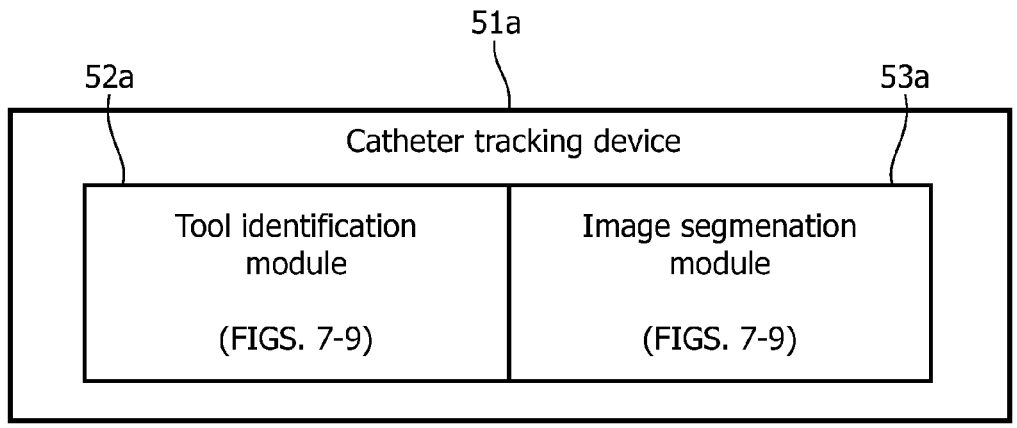
FIGS. 4-6 illustrate various embodiments of a tool tracking device in accordance with the present invention.

Specifically, FIG. 4 illustrates a catheter image tracking module 51*a* for implementing stages S63 and S64 in accordance with a process known herein as "tip detection mode" in view of the fact the manner by which the tip is detected may serve as a boundary constraint for subsequent image segmentation.

Figure 7:
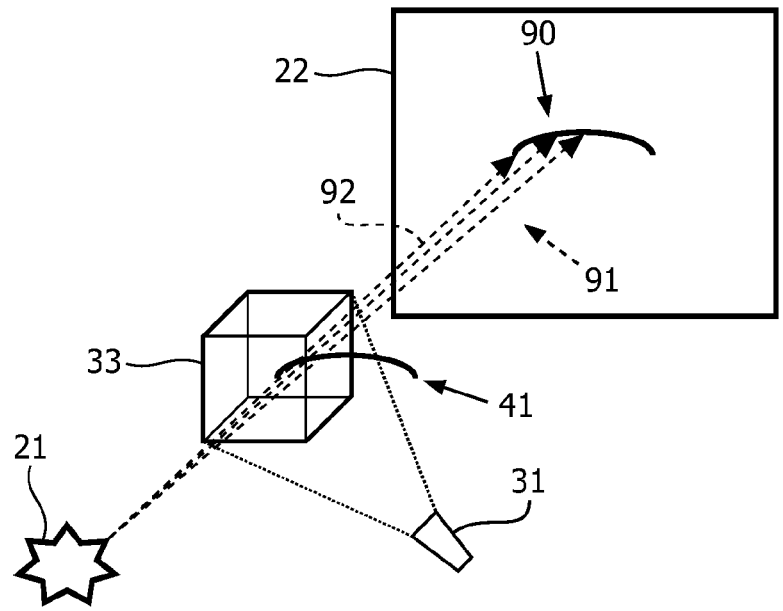
FIG. 7 illustrates an exemplary geometric relationship between an X-ray image and an ultrasound image in accordance with the present invention.

Generally, the "tip detection mode" utilizes a geometric relationship of an X-ray image and an ultrasound volume whereby a tool tip in the X-ray image corresponds to a line or a line set going through the ultrasound image after transformation using an X-ray/3D US registration. For example, as shown in FIG. 7, an X-ray projection 90 of a catheter 41 onto X-ray detector 22 via X-ray source 21 corresponds to a line set 91 of three (3) lines going through an ultrasound volume 33 after transformation using an X-ray/3D US registration. By using the illustrated geometric constraint, a six (6) degree of freedom ("DOF") catheter tracking problem [x, y, z, a, b, c], where xyz are translations and a, b, and c are rotations, is reduced into a four (4) DOF problem with [r, a, b, c], where r is a translation along a tracing line 92 associated with the catheter tip shown in FIG. 7. In practice, this catheter tracking problem may be efficiently solved by using a Kalman filter or particle filter based visual tracker, which has been extensively studied in computer vision. The reduction of search space to four (4) DOF significantly improves the step of the visual tracking algorithms as described below.

For example, a particle filter is used to illustrate how to build the catheter tracking module 51. Specifically, let X=[r, a, b, c] denote the state vector representing the location and the pose of catheter 41. The catheter tracking problem may be described by $p(X_t|V_{us}^t)$, i.e., to estimate state vector X using the ultrasound volume history. By using Bayes' rule, the following equation [1] is derived for tracking purposes:

$$p(X_t|V_{us}^t) = p(V_{us}^t|X_t)\int p(X_t|X_{t-1})p(X_{t-1}|V_{us}^{t-1})dX_{t-1} \quad [1]$$

Figure 8:
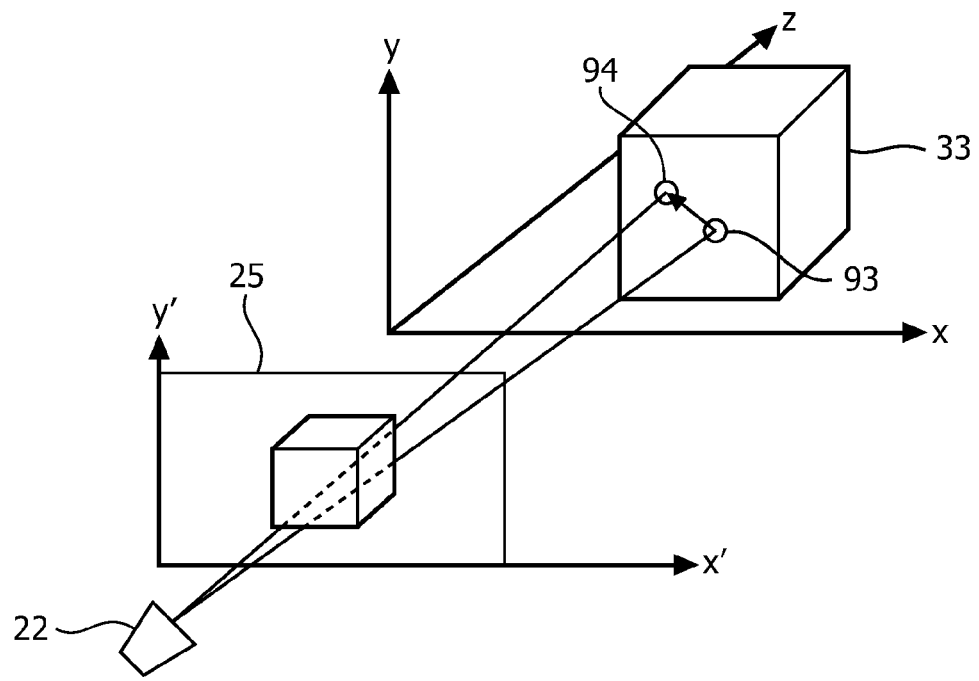
FIG. 8 illustrates an exemplary tool tip movement within an ultrasound image in accordance with the present invention.

By assuming the dynamic change from $X_{t-1}$ to $X_t$ as shown in FIG. 8 from a point 93 to a point 94 in 3D US volume 32 follows some distribution $p(X_t|X_{t-1})$, the particles sampled from the previous 3D US volume $p(X_{t-1}|V_{us}^{t-1})$ may be propagated to the next frame, where the fitness of an estimated tool tip to the current 3D US frame is measured by $p(V_{us}^t|X_t)$. By applying the geometric constraint from a single X-ray image 25 as shown in FIG. 8, the number of variables in the state vector X is reduced from six (6) to (4), which in turn reduces the number of samples used in the particle filter and shortens the tracking time by one-third (⅓) for an equivalent tracking accuracy compared to the unconstrained tracking in 3D US. In other words, with the same computational time, the proposed scheme can use more samples to make the catheter visualization in 3D US volume 32 more accurate and more robust.

Figure 9:
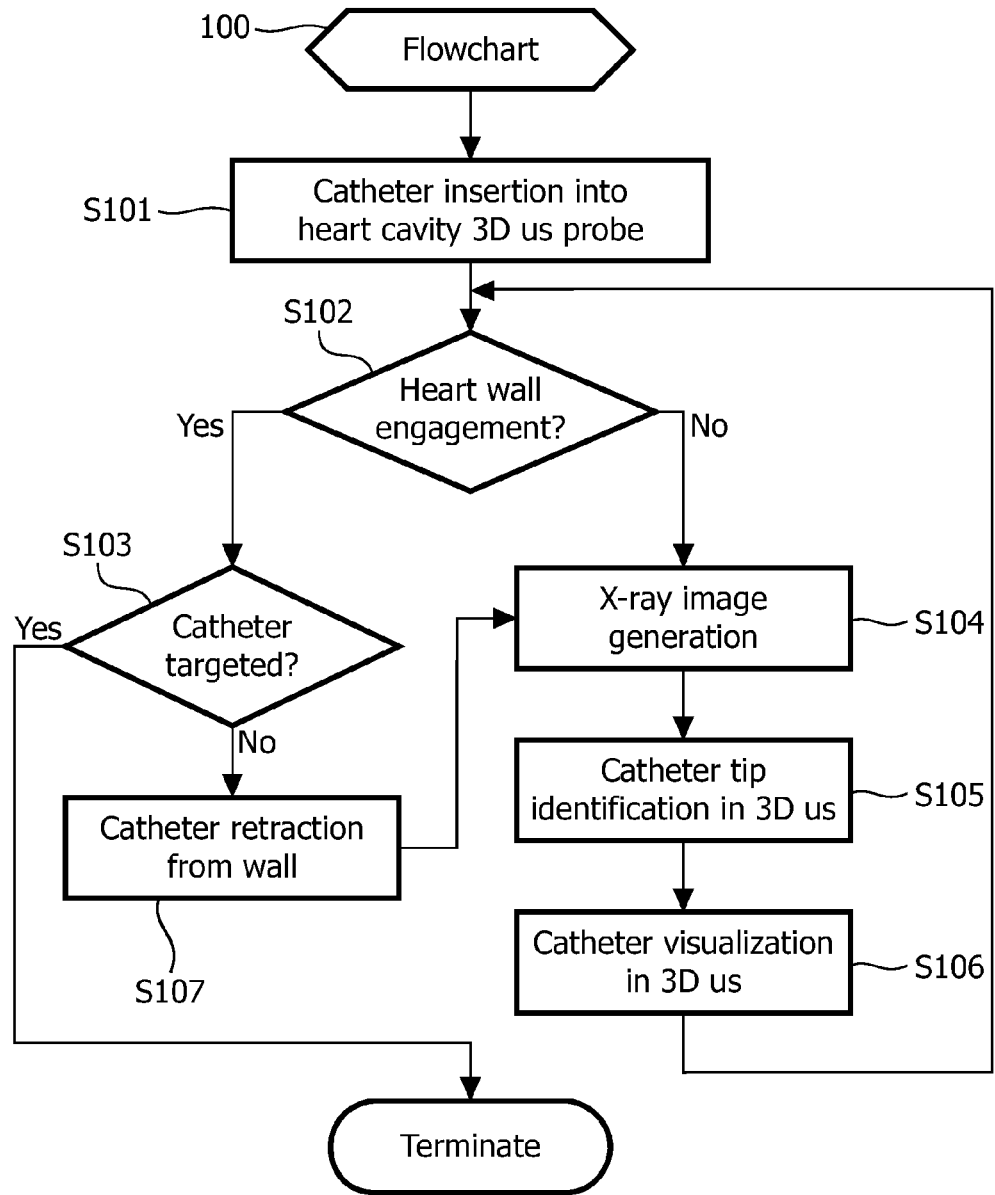
FIG. 9 illustrates a flowchart representative of one embodiment of a cardiac interventional procedure incorporating one embodiment of a tool tracking method in accordance with the present invention.

FIG. 9 illustrates a flowchart 100 representative of a cardiac interventional procedure incorporating the "tip detection mode" of the present invention via a tracking loop including stages S104-S106 of flowchart 100.

Specifically, stage S104 encompasses a generation of a single X-ray image of the heart cavity during a 3D US probe of the heart cavity. The single X-ray image is utilized by tool identification module 52a during stage S105 to identify the tip of the catheter in an ultrasound image of the heart cavity in one time phase or ECG phase.

In one embodiment of stage S105, the tip of the catheter is manually identified in a ultrasound image via a user input of the 3D US imaging system and a line extending from the X-ray source through 3D US volume to the catheter tip as projected on the X-ray detector is determined.

In a second embodiment of stage S105, the tip of the catheter is manually identified in the X-ray image via a user input of the X-ray image system and then mapped to the ultrasound image based on the X-ray/3D US registration. Additionally, a line extending from the X-ray source through 3D US volume to the catheter tip as projected on the X-ray detector is determined.

In a third embodiment of stage S105, the tip of the catheter is automatically identified in the X-ray image via a known template matching algorithm and then mapped to the ultrasound image based on the X-ray/3D US registration. Again, a line extending from the X-ray source through 3D US volume to the catheter tip as projected on the X-ray detector is determined.

In a fourth embodiment of stage S105, the catheter tip may be automatically detected in the ultrasound image using learning based techniques, where the appearance model can come from manual identification of catheter tip in sample 3D US images or from biplane X-ray images. In this appearance modelling process, 3D image patches are first extracted from the training 3D US volumes around the identified catheter tip. Each patch is reshaped into a vector and may be considered as a column of a matrix M. The singular value decomposition ("SVD") may be applied to the constructed matrix to extract the principal components U of the training patches. That is $M=U\Sigma V^T$.

During the detection process, the search is performed along the line back projected from the identified catheter tip in X-ray image to the 3D US volume. For each search location, a patch $I_p$ with the same size as the training patch is extracted. The patch can then be decomposed into $b=U^T I_p$ and the distance from the patch to the learned model is measured $\|b\|^2$. The catheter tip location may be detected as the point with the smallest distance.

Stage S106 encompasses image segmentation module 53a visualizing the 3D shape of the catheter within the ultrasound image. In practice, the present invention does not impose any restrictions or limitations to the segmentation of the catheter for visualization purposes. Nonetheless, during stage S106, the back-projected line or line set may serve as a boundary constraint for the catheter segmentation in the ultrasound image, i.e. the catheter tip has to be located somewhere along this line or line set. The catheter segmentation may be further constraint by the dimensions of the ultrasound image. Additionally, a priori knowledge of the catheter shape may be further used to determine statistically likely poses given the before mentioned boundary conditions.

One advantage of the execution of the tracking loop stages S104-S106 is the use of a monoplane X-ray imaging system.

Referring to on overall execution of flowchart 100, a stage S101 of flowchart 100 encompasses an insertion of a catheter into a heart cavity. Upon the insertion, a 3D US probe (e.g., probe 31 shown in FIG. 1) is utilized to selectively trigger the tracking loop as needed. Specifically, if the 3D US probe illustrates the catheter is at the heart wall and on target, then flowchart 100 from stage S101 through stages S102 and S103 to termination. Otherwise, if the 3D US probe illustrates the catheter is not at the heart wall during stage S102, then tracking loop stages S104-S106 are executed. Alternatively, if the 3D US probe illustrates the catheter is not on target at the heart wall during stage S103, then the catheter is retracted during a stage S107 prior to an execution of tracking loop stages S104-S106.

Figure 5:
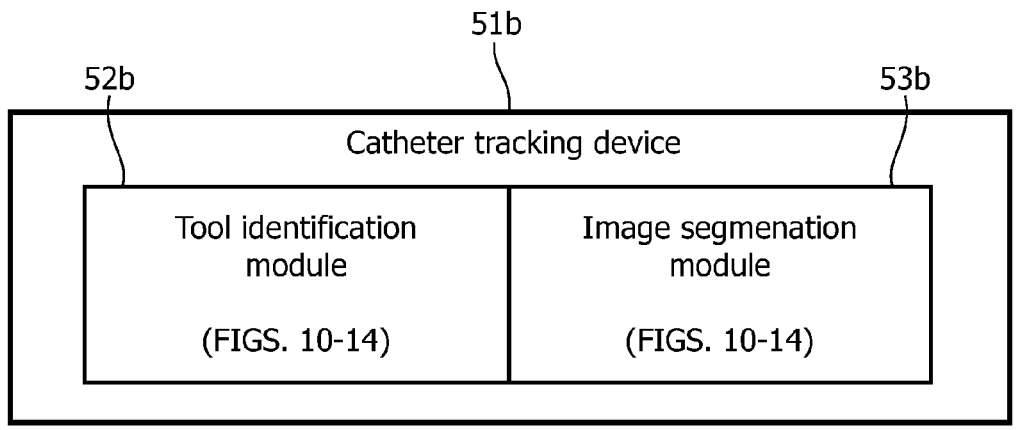

FIG. 5 illustrates a catheter image tracking module 51b for implementing stages S63 and S64 (FIG. 2) in accordance with a process known herein as "graph-cut segmentation mode" in view of the fact the manner by which catheter is segmented is based on a graph-cut method.

Figure 10:
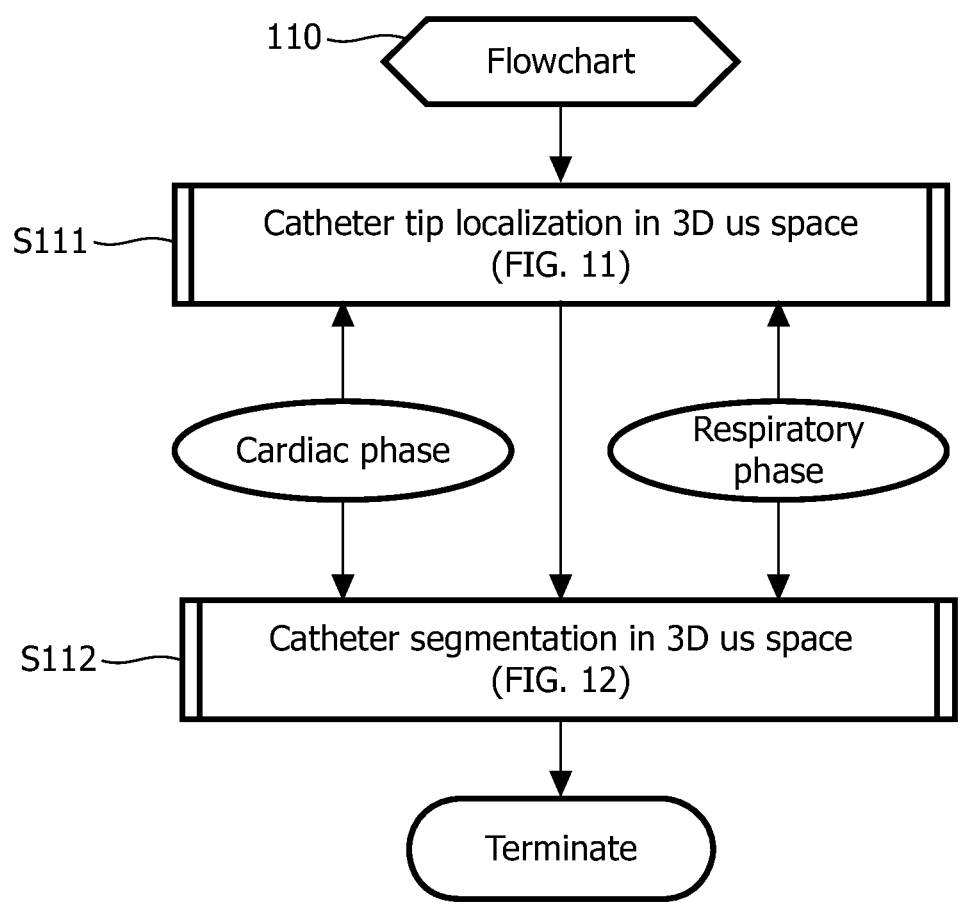
FIG. 10 illustrates a flowchart representative of a second embodiment of a tool tracking method in accordance with the present invention.

Generally, the "graph-cut segmentation mode" implements a flowchart 110 shown in FIG. 10 involving a catheter tip location in 3D US volume space during a stage S111 and a catheter segmentation in 3D US volume space during a stage S112.

In one embodiment of stage S111, the catheter tip may be manually identified in the 3D US volume space.

Figure 11:
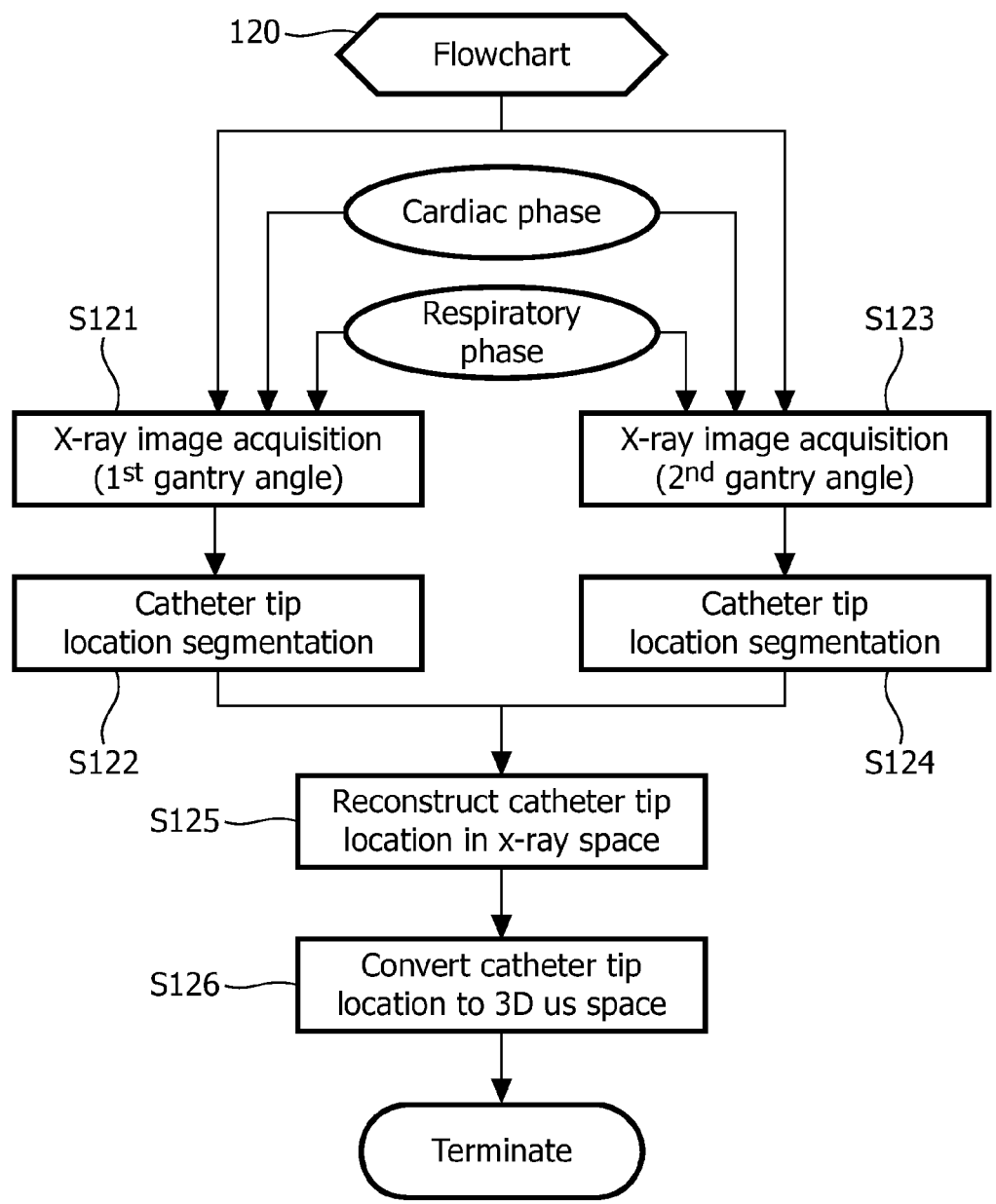
FIG. 11 illustrates a flowchart representative of one embodiment of a tool localization method in accordance with the present invention.

In a more reliable second embodiment of stage S111, a flowchart 120 representative of a catheter tip localization method of the present invention as shown in FIG. 11 is executed.

Referring to FIG. 11, upon the catheter being inserted within an anatomical region, a stage S121 of flowchart 120 encompasses an X-ray image acquisition of the catheter at a $1^{st}$ gantry angle during a specified cardiac phase (e.g., an end diastole phase) and a specified respiratory phase (e.g., an end respiratory phase) using known cardiac and respiratory gating techniques and a stage S122 of flowchart 120 encompasses a manual or automatic segmentation of the catheter tip in the X-ray image acquired during stage S121.

For a monoplane X-ray imaging system, a stage S123 of flowchart 120 encompasses an X-ray image acquisition of the catheter at a 2nd gantry angle during the same specified cardiac phase and the same specified respiratory phase using known cardiac and respiratory gating techniques and a stage S124 of flowchart 120 encompasses a manual or automatic segmentation of the catheter tip in the X-ray image acquired during stage S123.

For a biplane X-ray imaging system, stages S121/S122 and stages S123/S124 may be executed simultaneously.

For either X-ray imaging system, a corresponding 3D location of the catheter tip in the 2D X-ray coordinate system is reconstructed during a stage S125 of flowchart 120. In one embodiment of stage S125, a known epipolar constraint is utilized to reconstruct the 3D location of the catheter tip in the 2D X-ray coordinate system.

Thereafter, during a stage S126 of flowchart 120, a reconstructed 2D X-ray coordinate location of the catheter tip is converted into a 3D US real-time coordinate location using system calibration and real-time tracking. In one embodiment of stage S126, a manual alignment is used as the basis for the conversion. In a second embodiment of stage S126, a known electromagnetic tracking technique is used as the basis for the conversion.

Referring back to FIG. 10, flowchart 110 facilitates an execution of a flowchart 150 (FIG. 14) during stage S112.

Flowchart 150 is premised on a minimization of the following energy functional [2]:

$$\{x_p\} = \min_{\{x_p\}} \sum_p D_p(x_p) + \sum_{p \sim q} w_{pq}[x_p \neq x_q] \qquad [2]$$

where $x_p$ is the label of the pixel p and p~q indicates that the pixels p and q are neighbors. The first term of the energy functional $D_p(x_p)$ describes the cost of assigning a pixel to foreground or to background based on its label. The cost of assigning a pixel to the foreground is chosen as the absolute difference between the filter response $f_p$ at that pixel and the minimum filter response $\epsilon$ of the image. This cost gets its minimum value at the pixels inside the catheter as the filter that highlights the catheter gives its lowest response at those pixels. In a similar way, the cost of assigning a pixel to background is chose as the absolute difference between the filter response $f_p$ at that pixel and the mean filter response $\mu$ of the image.

On the other hand, the second pair wise part works as a regularization term. When two neighboring pixels p and q, have different labels $x_p$ and $x_q$, the predicate $[x_p \neq x_q]$ takes the value 1 and $w_{pq}$ accumulates to the energy, otherwise it takes the value 0 and $w_{pq}$ has no contribution to the energy. As a natural choice for $w_{pq}$ that favors the assignment of the same label to the nearby pixels with similar filter response, the similarity measure $w_{pq} = e^{-B|f_p - f_q|}$ may be utilized.

Figure 12:
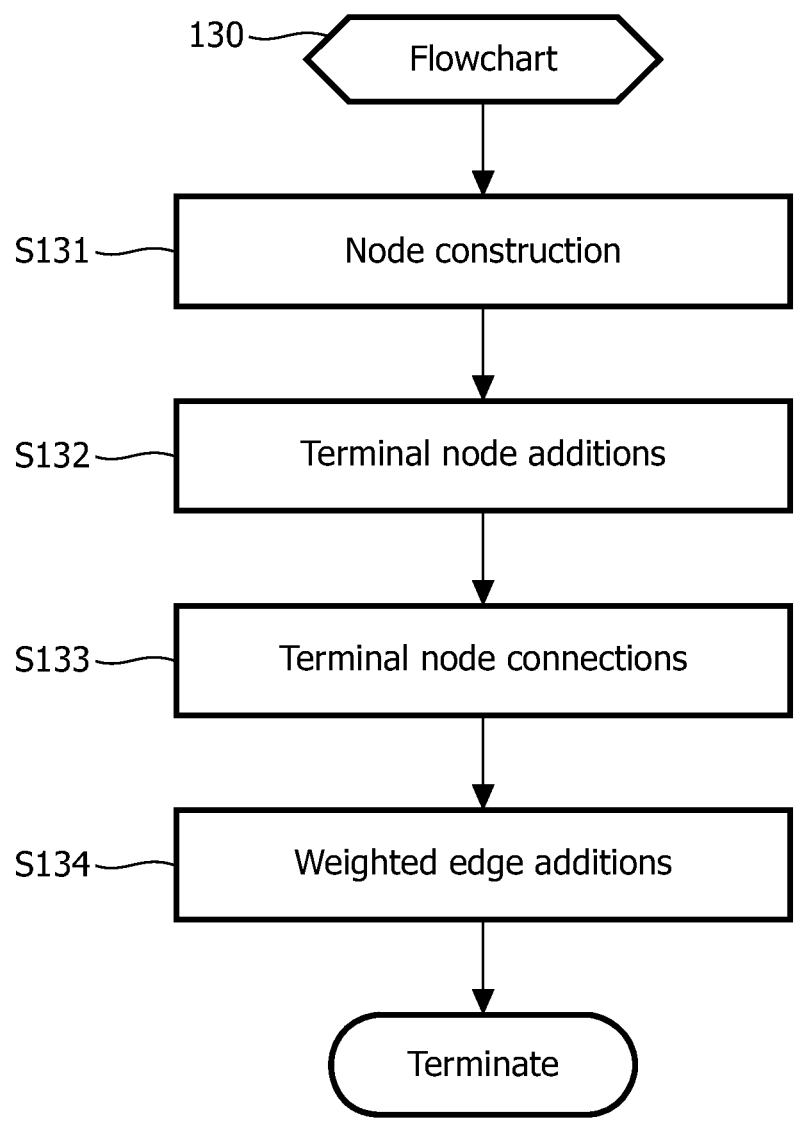
FIG. 12 illustrates a flowchart representative of one embodiment of a weighted graph construction method in accordance with the present invention.
Figure 13:
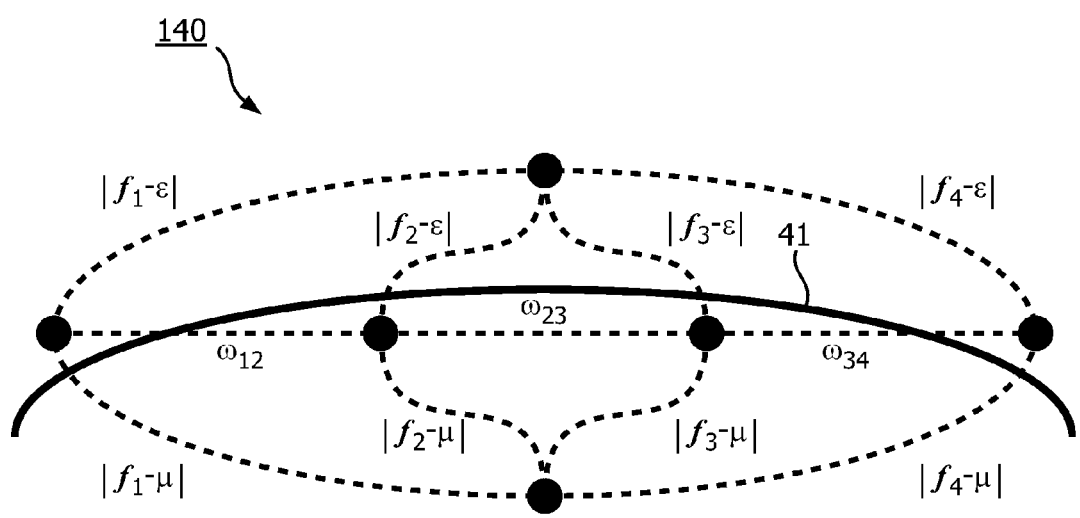
FIG. 13 illustrates an exemplary weighted graph corresponding to an energy function in accordance with the present invention.

To find the global minimum of equation [2], a flowchart 130 as shown in FIG. 12 is executed for constructing a weighted graph, such as, for example, a weighted graph 140 shown in FIG. 13. Referring to FIGS. 12 and 13, a stage S131 of flowchart 130 encompasses a construction of a node to the graph for each pixel. As this is a binary optimization problem, a stage S132 of flowchart 130 encompasses an addition of two (2) terminal nodes s and t representing background and foreground, respectively. Next, a stage S133 of flowchart 130 encompasses a connection of terminal node s to each node representing pixels and assignment of the weight, and a connection of terminal node t to each node and assignment of the weight $|f_p - \mu|$ to those edges. Finally, a stage S134 of flowchart 130 encompasses an addition of edges that connect the nodes representing neighboring pixels, and assignment of the weight $w_{pq}$ to the edges.

Figure 14:
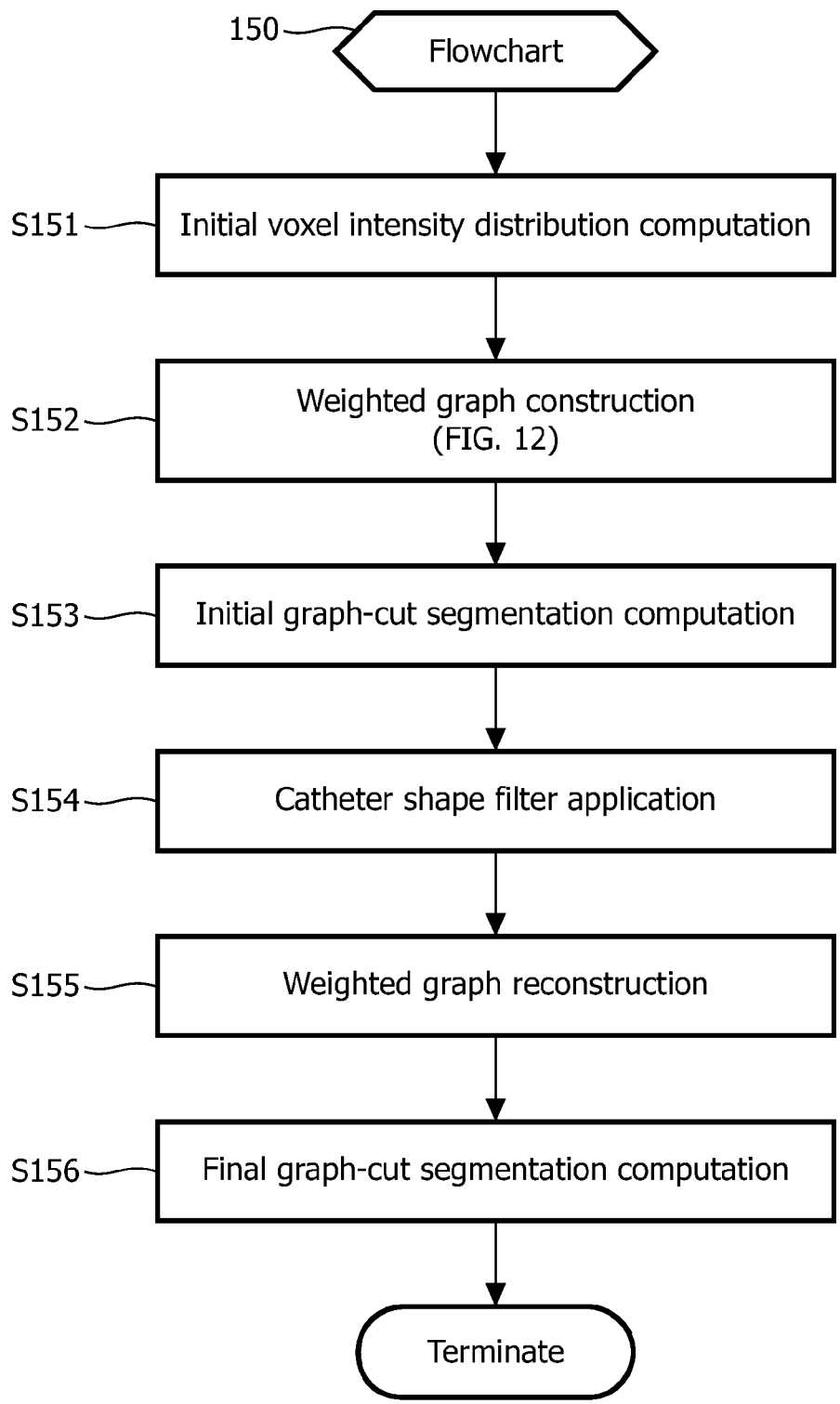
FIG. 14 illustrates a flowchart representative of one embodiment of an image segmentation method in accordance with the present invention.

Referring now to FIG. 14, flowchart 150 is executed for segmenting the catheter in the 3D US volume space. Specifically, a localized tool tip in 3D US volume space as determined by flowchart 120 (FIG. 11) is utilized as the initial seed point and a stage S151 of flowchart 150 encompasses a generation of a small neighborhood around the identified tool tip to compute a probability distribution function (PDF) of the catheter intensity. Next, a stage S152 of flowchart 150 encompasses a computation of the term $D_p(x_p)$ for equation [2] to assign the weight to each terminal link for purposes of constructing the weighted graph, and a stage S153 of flowchart 150 encompasses an application of a graph-cut to the constructed graph to obtain an initial segmentation.

The initial segmentation may not be ideal, because not only the catheter itself but also some other structure around it with similar appearance may be included into the segmentation. Thus, a stage S154 of flowchart 150 encompasses an application of a catheter shape filter to refine the initial segmentation. The catheter shape filter is designed to exploit the tubular structure of the catheter and may be a $2^{nd}$ derivative of 2D Gaussian kernel with 3D orientation in the design. In one embodiment, an orientation of the filter is set by computing the principal direction of the initial segmentation.

Upon completion of stage S154, a stage S155 of flowchart 150 encompasses a construction of a new 3D graph the same manner as stage S152. A final catheter segmentation is done by applying graph-cut again on this new graph during a stage S156 of flowchart 150.

Figure 6:
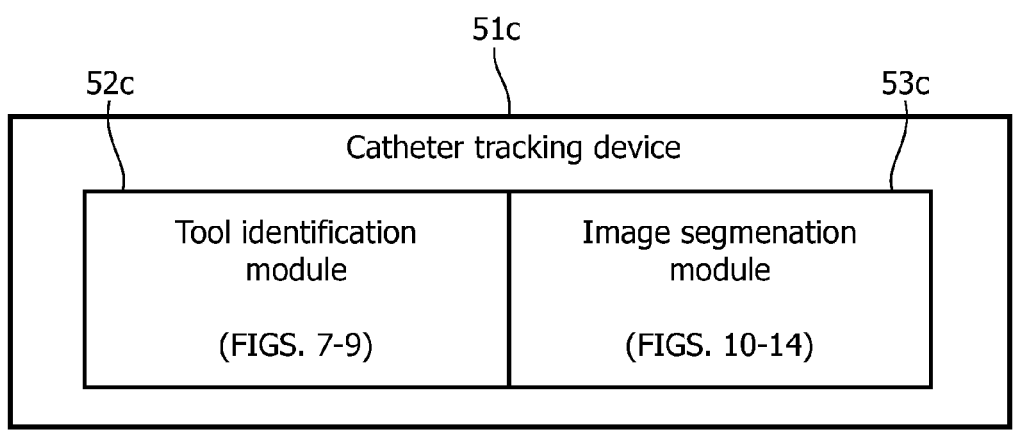

From the description of FIGS. 7-14, those having ordinary skill in the art will appreciate the "tip detection mode" and the "graph-cut segmentation mode" of catheter tracking device 51a (FIG. 4) and catheter tracking device 51b (FIG. 5), respectively. FIG. 6 illustrates a catheter image tracking module 51c for implementing stages S63 and S64 in accordance with a combination of "tip detection mode" as executed by a tool detection module 52c and the "graph-cut segmentation mode" as executed by the image segmentation module 53c.

From the description of FIGS. 1-14, those having skill in the art will have a further appreciation on how to implement a tool tracking method for any application in accordance with the present invention.

In practice, any number of X-ray imaging device 20, 3D US imaging device 30 and a tool tracking device may be integrated into a single device.

While various exemplary embodiments of the present invention have been illustrated and described, it will be understood by those skilled in the art that the exemplary embodiments of the present invention as described herein are illustrative, and various changes and modifications may be made and equivalents may be substituted for elements thereof without departing from the true scope of the present invention. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. An image-guided system, comprising:
an X-ray imaging device having an X-ray source and an X-ray detector, the X-ray imaging device being configured to generate at least one X-ray image illustrating a tool within an anatomical region;
an ultrasound imaging device configured to acquire a three-dimensional (3D) ultrasound (US) volume, the 3D US volume including an ultrasound image illustrating the tool within the anatomical region in the 3D US volume; and
a tool tracking device configured to:
perform a registration of the ultrasound image with the X-ray image,
localize a portion of the tool as located within the ultrasound image based on an identification of the portion of the tool as located within the at least one X-ray image by localizing the portion of the tool along at least one line extending from the X-ray source to a projection of the tool on the X-ray detector through the 3D US volume after the registration of the ultrasound image with the X-ray image,
perform an execution of an image segmentation of an entirety of the tool as located within the ultrasound image relative to a localization of the portion of the tool as located within the ultrasound image, and track the portion of the tool as located within the ultrasound image from a first location in a previous 3D US volume acquired in a previous time to a second location in a next 3D US volume acquired in a next time which is after the previous time by estimating a state vector X using an ultrasound volume history to propagate samples from the previous 3D US volume to the next 3D US volume, wherein the state vector X includes location information and pose information of the tool, the location information being confined to single translation along the at least one line extending from the X-ray source to the projection of the tool on the X-ray detector through the 3D US volume.

2. The image-guided system of claim 1, wherein the tool is a catheter, and wherein the portion of the tool is a tip of the tool.

3. The image-guided system of claim 1, wherein the X-ray imaging device is one of a group including a monoplane X-ray imaging device and a bi-plane X-ray imaging device.

4. The image-guided system of claim 1, wherein the execution of the image segmentation of the entirety of the tool as located within the ultrasound image relative to the localization of the portion of the tool as located within the ultrasound image includes:
   constructing an initial weighted energy graph; and
   executing a graph-cut segmentation of the initial weighted energy graph.

5. The image-guided system of claim 4, wherein the execution of the image segmentation of the entirety of the tool as located within the ultrasound image relative to the localization of the portion of the tool as located within the ultrasound image further includes:
   applying a shape filter to the graph-cut segmentation of the initial weighted energy graph;
   constructing a final weighted energy graph as a function of the application of the shape filter to the graph-cut segmentation of the initial weighted energy graph; and
   executing a graph-cut segmentation of the final weighted energy graph.

6. The image-guided system of claim 1, wherein the at least one line serves as at least one boundary constraint for the execution of the image segmentation of the entirety of the tool as located within the ultrasound image and the localized portion of the tool is used as an initial seed point for the image segmentation within the ultrasound image.

7. A tool tracking device for tracking a tool within an anatomical region, the tool tracking device comprising:
   a tool identification module configured to:
   perform a registration of an ultrasound image included in a three-dimensional (3D) ultrasound (US) volume with an X-ray image illustrating the tool within the anatomical region
   localize a portion of the tool as located within the ultrasound image illustrating the tool within the anatomical region based on an identification of the portion of the tool as located within the X-ray image illustrating the tool within the anatomical region by localizing the portion of the tool along at least one line extending from an X-ray source of an X-ray imaging device to a projection of the tool on an X-ray detector of the X-ray imaging device through the 3D US volume after the registration of the ultrasound image with the X-ray image, and
   track the portion of the tool as located within the ultrasound image from a first location in a previous 3D US volume acquired in a previous time to a second location in a next 3D US volume acquired in a next time which is after the previous time by estimating a state vector X using an ultrasound volume history to propagate samples from the previous 3D US volume to the next 3D US volume, wherein the state vector X includes location information and pose information of the tool, the location information being confined to single translation along the at least one line extending from the X-ray source to the projection of the tool on the X-ray detector through the 3D US volume; and an image segmentation module configured to perform an execution of an image segmentation of an entirety of the tool as located within the ultrasound image relative to a localization of the portion of the tool as located within the ultrasound image.

8. The tool tracking device of claim 7, wherein the tool is a catheter, and wherein the portion of the tool is a tip of the tool.

9. The tool tracking device of claim 7, wherein the execution of the image segmentation of the entirety of the tool as located within the ultrasound image relative to the localization of the portion of the tool as located within the ultrasound image further includes:
   constructing an initial weighted energy graph; and
   executing a graph-cut segmentation of the initial weighted energy graph.

10. The tool tracking device of claim 9, wherein the execution of the image segmentation of the entirety of the tool as located within the ultrasound image relative to the localization of the portion of the tool as located within the ultrasound image further includes:
    applying a shape filter to the graph-cut segmentation of the initial weighted energy graph;
    constructing a final weighted energy graph as a function of the application of the shape filter to the graph-cut segmentation of the initial weighted energy graph; and
    executing a graph-cut segmentation of the final weighted energy graph.

11. The tool tracking device of claim 7, wherein the at least one line serves as at least one boundary constraint for the execution of the image segmentation of the entirety of the tool as located within the ultrasound image and the localized portion of the tool is used as an initial seed point for the image segmentation within the ultrasound image.

12. An image-guided method for tracking a tool within an anatomical region, comprising acts of:
    generating by an X-ray imaging device an X-ray image illustrating the tool within an anatomical region, the X-ray imaging device having an X-ray source and an X-ray detector;
    acquiring by an ultrasound imaging device a three-dimensional (3D) ultrasound (US) volume, the 3D US volume including an ultrasound image illustrating the tool within the anatomical region in the 3D US volume;
    registering the ultrasound image with the X-ray image;
    localizing by a tool tracking device a portion of the tool as located within the ultrasound image based on an identification of the portion of the tool as located within the X-ray image by localizing the portion of the tool along at least one line extending from the X-ray source to a projection of the tool on the X-ray detector through the 3D US volume after the act of registering the ultrasound image with the X-ray image;
    executing by the tool tracking device an image segmentation of an entirety of the tool as located within the ultrasound image relative to a localization of the portion of the tool as located within the ultrasound image; and tracking the portion of the tool as located within the ultrasound image from a first location in a previous 3D US volume acquired in a previous time to a second location in a next 3D US acquired in a next time which is after the previous time volume by estimating a state vector X using an ultrasound volume history to propagate samples from the previous 3D US volume to the next 3D US volume, wherein the state vector X includes location information and pose information of the tool, the location information being confined to single translation along the at least one line extending from the X-ray source to the projection of the tool on the X-ray detector through the 3D US volume.

13. The image-guided method of claim 12, wherein the executing act includes acts of:
constructing an initial weighted energy graph; and
executing a graph-cut segmentation of the initial weighted energy graph.

14. The image-guided method of claim 13, wherein the execution of the image segmentation of the entirety of the tool as located within the ultrasound image relative to the localization of the portion of the tool as located within the ultrasound image further includes:

applying a shape filter to the graph-cut segmentation of the initial weighted energy graph;

constructing a final weighted energy graph as a function of the application of the shape filter to the graph-cut segmentation of the initial weighted energy graph; and executing a graph-cut segmentation of the final weighted energy graph.

15. The image-guided method of claim 12, wherein the at least one line serves as at least one boundary constraint for the execution of the image segmentation of the entirety of the tool as located within the ultrasound image and the localized portion of the tool is used as an initial seed point for the image segmentation within the ultrasound image.

* * * * *